(12) United States Patent
Burry et al.

(10) Patent No.: US 8,298,553 B2
(45) Date of Patent: Oct. 30, 2012

(54) PERSONAL CARE COMPOSITION

(75) Inventors: Jason Shaun Burry, Wirral (GB);
Richard Livesey Evans, Wirral (GB);
Caroline Alexandra Hall, Wirral (GB);
Ezat Khoshdel, Wirral (GB); Colina Mackay, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 124 days.

(21) Appl. No.: 12/745,975

(22) PCT Filed: Nov. 11, 2008

(86) PCT No.: PCT/EP2008/065287
§ 371 (c)(1),
(2), (4) Date: Jun. 3, 2010

(87) PCT Pub. No.: WO2009/071422
PCT Pub. Date: Jun. 11, 2009

(65) Prior Publication Data
US 2010/0249080 A1    Sep. 30, 2010

(30) Foreign Application Priority Data
Dec. 6, 2007   (EP) ..................................... 07122472

(51) Int. Cl.
*A61K 9/00* (2006.01)
*A61K 8/18* (2006.01)

(52) U.S. Cl. ........................................ 424/400; 424/70.1

(58) Field of Classification Search .................. None
See application file for complete search history.

(56) References Cited

U.S. PATENT DOCUMENTS

| | | |
|---|---|---|
| 3,958,581 A | 5/1976 | Abegg et al. |
| 3,962,418 A | 6/1976 | Birkofer |
| 4,009,256 A | 2/1977 | Nowak, Jr. et al. |
| 4,275,055 A | 6/1981 | Nichtigal et al. |
| 5,194,639 A | 3/1993 | Connor et al. |
| 5,506,224 A * | 4/1996 | della Valle et al. ........... 514/182 |
| 6,548,550 B1 * | 4/2003 | Comelli et al. ............... 514/625 |
| 2002/0182159 A1* | 12/2002 | McGlone et al. ............... 424/65 |
| 2003/0049220 A1* | 3/2003 | Bailey et al. ................. 424/70.1 |
| 2004/0018954 A1* | 1/2004 | Su et al. ............................ 512/1 |
| 2005/0009902 A1* | 1/2005 | Miyaji et al. .................. 514/453 |
| 2006/0216251 A1* | 9/2006 | Morariu .......................... 424/59 |
| 2006/0241175 A1* | 10/2006 | Schwarz et al. ............... 514/458 |
| 2007/0048360 A1* | 3/2007 | Carrara et al. ................ 424/443 |
| 2007/0224261 A1* | 9/2007 | Draper .......................... 424/452 |

FOREIGN PATENT DOCUMENTS

| | | |
|---|---|---|
| EP | 0 336 850 | 10/1989 |
| EP | 1406576 A1 * | 4/2004 |
| EP | 1 785 130 | 5/2007 |
| WO | WO9206154 A1 | 4/1992 |
| WO | WO9522311 | 8/1995 |
| WO | WO9631188 | 10/1996 |
| WO | 97/03637 | 2/1997 |
| WO | 98/51283 | 11/1998 |
| WO | 01/82890 | 11/2001 |
| WO | WO 0182890 A1 * | 11/2001 |
| WO | 02/64106 | 6/2002 |
| WO | 03/007901 | 1/2003 |
| WO | 2005/018530 | 3/2005 |
| WO | 2005/117981 | 12/2005 |
| WO | 2006/096955 | 9/2006 |
| WO | WO 2008107179 A1 * | 9/2008 |

OTHER PUBLICATIONS

PCT International Search Report in PCT application PCT/EP2008/065287—May 8, 2009.
European Search Report in EP 07 12 2472—Jun. 9, 2006.
PCT International Search Report in PCT application PCT/EP2008/064926—May 20, 2009.
European Search Report in EP 07 12 2471—Jun. 5, 2006.
Co-pending Application: Applicant: Burry et al., U.S. Appl. No. 12/745,970, filed Jun. 3, 2010.

* cited by examiner

*Primary Examiner* — Robert A Wax
*Assistant Examiner* — Olga V Tcherkasskaya
(74) *Attorney, Agent, or Firm* — Ronald A. Koatz

(57) ABSTRACT

A personal care composition comprising a eutectic mixture, the eutectic mixture comprising a CB receptor activating agent, in which the CB receptor is preferably palmitoylethanolamide. A method of mitigating scalp itch.

12 Claims, 1 Drawing Sheet

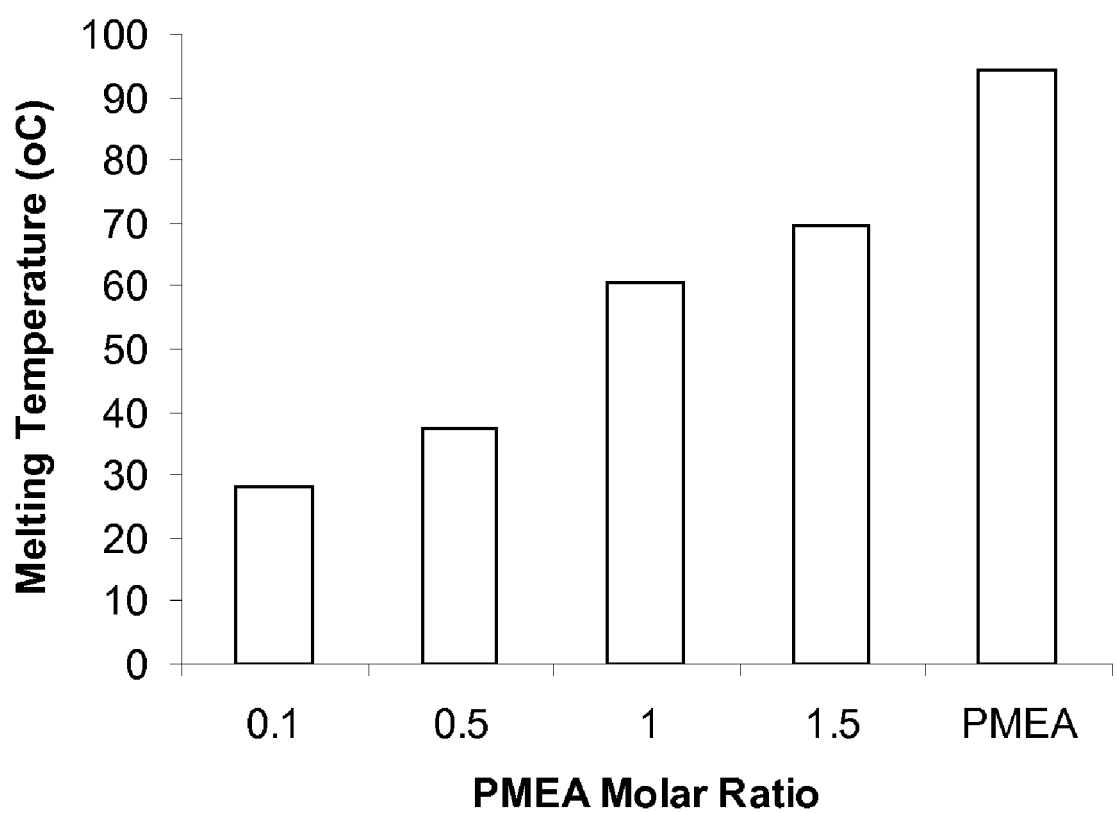

PERSONAL CARE COMPOSITION

This invention relates personal care compositions and in particular to hair and/or scalp care compositions. The invention also relates to the use of these compositions for the treatment of scalp itch.

Many personal care compositions are used to deposit benefit agents on the skin/scalp or hair, however efficient deposition of these benefit agents can pose a problem, especially in rinse off compositions.

Eutectic mixtures have been used in WO 98/51283 to aid the transdermal delivery of a pharmacologically active drug.

Eutectic mixtures of active substances, such as local anaesthetic mixtures, are described for use in pharmaceutical and cosmetic compositions in WO 2005/018530. Such mixtures are said to provide an improved dermal penetration profile.

The present inventors have found that certain eutectic mixtures can be used to enhance deposition of CB receptor activating agents and so mitigate scalp itch.

According to the invention there is provided a personal care composition comprising a eutectic mixture, the eutectic mixture comprising a CB receptor activating agent.

In another aspect the invention relates to a method of depositing CB receptor activating agent onto the scalp or skin in which the CB receptor activating agent is in the form of a eutectic mixture.

The invention also relates to a method of scalp itch comprising the step of applying to the hair and/or scalp a composition as described above.

A eutectic mixture of two or more eutectic-forming solids shows, upon intimate admixture of the solids, a homogeneous liquid phase above the melting point of the higher melting component. A plot of melting point versus relative composition of the two eutectic-forming solids displays a minimum point between two intersecting lines at which a homogeneous liquid phase coexists with each of the respective homogeneous solid phases. This point is known as the eutectic point or eutectic temperature.

The present invention relates to a eutectic mixture comprising a CB receptor activating agent.

Examples of suitable CBR activating agents include:—
2-arachidonyl-glycerol
1-arachidonyl-glycerol
3-arachidonyl-glycerol
2-linoleoyl-glycerol
2-linolenoyl-glycerol
2-eicosatrienoyl-glycerol
2-eicosatetraenoyl-glycerol
2-eicosapentenoyl-glycerol
2-eicosahexaenoyl-glycerol
Palmitoylethanolamide
(6aR)-trans-3-(1,1-Dimethylheptyl)-6a,7,10,10a-tetrahydro-1-hydroxy-6,6-dimethyl-6H-dibenzo[b,d]pyran-9-methanol, sometimes called HU-210 herein;
Indomethacin morpholinylamide sometimes abbreviated to IMMA herein;
mesylate: (R)-(+)-[2,3-Dihydro-5-methyl-3-(4-morpholinylmethyl)pyrrolo[1,2,3-de]-1,4-benzoxazin-6-yl]-1-naphthalenylmethanone, sometimes called WIN55212-2 herein;
(−)-cis-3-[2-Hydroxy-4-(1,1-dimethylheptyl)phenyl]-trans-4-(3-hydroxypropyl)cyclohexanol, sometimes called CP55940 herein;
R-(+)-Methanandamide: [R-(all-Z)]-N-(2-Hydroxy-1-methylethyl)-5,8,11,14-eicosatetraenamide;
Arachidonyl-2'-chloroethylamide: (all Z)—N-(2-cycloethyl)-5,8,11,14-eicosatetraenamide); and
Arachidonylcyclopropylamide: (all Z)—N-(cyclopropyl)-5,8,11,14-eicosatetraenamide.

Naturally occurring precursors of said CBR activating agents can also be employed herein, generating the activating agent for example by hydrolysis on the skin.

Mixtures of two or more of said CBR activating agents can be employed herein.

Particularly preferred is palmitoylethanolamide.

The amount of CBR activating agent in the compositions of the invention is preferably selected in the range from at least 0.01 wt %, and often to not more than 10 wt % of the total composition, more preferably from 0.05% to 5 wt %. In a number of practical formulations, the concentration of CBR activating agent is not more than 5%, and particularly from 0.25 to 2 wt %.

Preferably the composition comprises menthol. Menthol is preferably present in the total composition at a level from 0.001 to 5 wt %, more preferably from 0.01 to 2 wt %.

A further component that is advantageous when used in the eutectic mixture is an organic acid. Preferred organic acids are lactic acid, glycolic acid, hydroxy acids (in particular citric, tartaric, malic), fatty acids, amino acids, hydroxyoctanoic acid, adipic acid, benzoic acids.

Particularly preferred organic acids are selected from the list consisting of salicylic acid, benzoic acid and mixtures thereof.

As an alternative to the organic acids mentioned above the eutectic mixture may comprise catechol and/or chrysin.

It is preferred if the molar ratio of palmitoyl ethanolamide/menthol/organic acid within the eutectic mixture is preferably from 0.1:1:1 to 2:1:1, and more preferably from 0.1:1:1 to 0.7:1:1.

Product Forms

Compositions of the present invention are typically personal care compositions, and it is preferred if they are compositions for topical application to the hair and/or scalp. They may be formulated as transparent or opaque emulsions, lotions, creams, pastes or gels.

Hair and/or scalp care compositions of the invention may be rinse off products or leave on products. Leave on products are intended not to be rinsed off the hair and/or the scalp of the user immediately after use (i.e., within at least the first 2 hours, preferably at least four hours, after application of the composition). Leave on products include, for example, lotions, creams and hair oils that are intended for topical application to the hair and/or the scalp. Rinse off products are intended to be substantially rinsed off the hair and/or the scalp of the user with water after use. Rinse off compositions include shampoos and hair conditioners, as well as hair and/or scalp treatment products which are intended to be left on the hair and/or scalp for up to half an hour, preferably 5 minutes, before being rinsed off.

Preferred product forms are shampoos and conditioners.

Rinse off compositions are preferred.

Shampoo Compositions

Shampoo compositions according to the invention will typically comprise one or more anionic cleansing surfactants which are cosmetically acceptable and suitable for topical application to the hair.

Anionic Cleansing Surfactant

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 percent by weight of the composition.

Co-Surfactant

Shampoo compositions according to the invention can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred blend of cleansing surfactants is a combination of ammonium lauryl ether sulphate, ammonium lauryl sulphate, PEG 5 cocamide and cocamide MEA (CTFA designations).

The shampoo composition can also optionally include one or more cationic co-surfactants included in an amount ranging from 0.01 to 10, more preferably from 0.05 to 5, most preferably from 0.05 to 2 percent by weight of the composition. Useful cationic surfactants are described here in below in relation to conditioner compositions.

The total amount of surfactant (including any co-surfactant, and/or any emulsifier) in shampoo compositions of the invention is generally from 5 to 50, preferably from 5 to 30, more preferably from 10 to 25 percent by weight of the composition.

Cationic Polymer

A cationic polymer is a preferred ingredient in shampoo compositions according to the invention, for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range. Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and copolymers of unsaturated carboxylic acids having from 3 to 5 carbon atoms, (as described in U.S. Pat. No. 4,009,256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

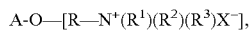

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 percent by weight of the composition.

When cationic conditioning polymer is present in a shampoo composition according to the invention, it is preferred if the copolymer is present as emulsion particles with a mean diameter ($D_{3,2}$ as measured by light scattering using a Malvern particle sizer) of 2 micrometers or less.

Hair Conditioner Compositions

Compositions in accordance with the invention may also be formulated as conditioners for the treatment of hair (typically after shampooing) and subsequent rinsing.

Hair conditioner compositions according to the invention will suitably comprise a cationic conditioning surfactant that is cosmetically acceptable and suitable for topical application to the hair.

Cationic Conditioning Surfactant

Examples of suitable cationic conditioning surfactants are those corresponding to the general formula:

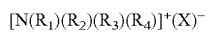

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferred cationic conditionings surfactants are monoalkyl quaternary ammonium compounds in which the alkyl chain length is C16 to C22.

Other preferred cationic conditioning surfactants are so-called dialkyl quaternary ammonium compounds in which R1 and R2 independently have an alkyl chain lengths from C16 to C22 and R3 and R4 have 2 or less carbon atoms.

Examples of suitable cationic surfactants include: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. A particularly useful cationic conditioning surfactant is cetyltrimethylammonium chloride, available commercially, for example as GENAMIN CTAC, ex Hoechst Celanese.

Salts of primary, secondary, and tertiary fatty amines are also suitable cationic conditioning surfactants. The alkyl groups of such amines preferably have from about 12 to about 22 carbon atoms, and can be substituted or unsubstituted.

Particularly useful are amido substituted tertiary fatty amines. Such amines, useful herein, include stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to H$^+$ from the acid is preferably from about 1:0.3 to 1:1.2, and more preferably from about 1:0.5 to about 1:1.1.

In the conditioners of the invention, the level of cationic conditioning surfactant is suitably from 0.01 to 10, preferably from 0.05 to 5, more preferably from 0.1 to 2 percent by weight of the total composition.

Fatty Materials

Hair conditioner compositions according to the invention preferably additionally comprise fatty materials.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Preferred fatty materials include cetyl alcohol, stearyl alcohol and mixtures thereof.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.1 to 5 percent by weight of the composition. The weight ratio of cationic surfactant to fatty material is suitably from 10:1 to 1:10, preferably from 4:1 to 1:8, optimally from 1:1 to 1:7, for example 1:3.

Hair conditioner compositions of the invention can also contain a cationic polymer. Suitable cationic polymers are described hereinabove in relation to shampoo compositions.

Hair oils are also suitable product forms according to the invention. Hair oils predominantly comprise water-insoluble oily conditioning materials. Lotions are aqueous emulsions comprising water-insoluble oily conditioning materials. Suitable surfactants can also be included in lotions to improve their stability to phase separation.

Compositions of this invention may contain any other ingredient normally used in hair treatment formulations.

Suspending Agents

Hair treatment compositions according to the invention such as shampoos suitably comprise from 0.1 to 5 wt % of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum.

Further Conditioning Agents

Hair treatment compositions according to the invention such as shampoos and conditioners suitably contain further conditioning agents such as silicone conditioning agents and non-silicone oily conditioning agents.

Suitable silicone conditioning agents include polydiorganosiloxanes, in particular polydimethylsiloxanes which have the CTFA designation dimethicone. Also suitable for use in compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning. Also suitable are functionalised silicones, particularly amino-functionalised silicones.

Suitable non-silicone oily conditioning agents are selected from hydrocarbon oils, fatty esters and mixtures thereof.

The further conditioning agent is suitably present in shampoo or conditioner compositions at a level of from 0.05 to 10, preferably from 0.2 to 5, more preferably from about 0.5 to 3 percent by total weight of further conditioning agent based on total weight of the composition.

The composition may further comprise an antidandruff agent. Suitable antidandruff agents include climbazole, ketaconazole and zinc salts. A preferred antidandruff agent is zinc pyrithione (ZnPTO).

Hair treatment compositions of the invention may contain other optional ingredients for enhancing performance and/or consumer acceptability, such as fragrance, dyes and pigments, pH adjusting agents, pearlescers or opacifiers, viscosity modifiers, preservatives, and natural hair nutrients such as botanicals, fruit extracts, sugar derivatives and amino acids.

Compositions of the invention preferably have an aqueous base.

The invention is further illustrated with reference to the following, non-limiting examples, in which all percentages are by weight based on total weight unless otherwise specified.

EXAMPLES

The following are lists of suitable eutectic mixtures for use with the invention:

TABLE 1

Molar ratios of triple active combinations containing palmitoyl ethanolamide, menthol, and an organic acid, that combine to form a eutectic mixture.

| Materials | | | Molar ratio |
|---|---|---|---|
| PMEA | Menthol | Phenol | 1:1:1 |
| PMEA | Menthol | Sacilcylic acid | 1:1:1 |
| PMEA | Menthol | Salicylic acid | 0.5:1:1 |

Preparation of Eutectic Mixture and Melting Point Determination

Palmotoylethanolamide, menthol and salicylic acid or phenol were initially combined in a 1:1:1 molar ratio, and the molar ratio of palmitoyl ethanolamide then further adjusted to determine the range of ratios over which eutectic mixtures could be formed. The formation of a eutectic mixture was confirmed by demonstrating a decrease in melting temperature of the mixture relative to that of the melting temperatures of the constituent actives individually.

The melting point of pure active samples (i.e. non-formulated actives) were determined using an Electrothermal Digital Melting Point measurement apparatus. Samples were held in glass capillary tubes and brought to a melt condition using a temperature ramp of 1° C./min. Melting temperature was measured when the sample formed a completely clear liquid.

FIG. 1 shows the melting point range of palmitoyl ethanolamide, menthol and salicylic acid eutectic mixtures containing different molar ratios of palmitoyl ethanolamide.

The following base shampoo was prepared:

Formula 1

| Ingredient | wt % |
|---|---|
| SLES-1EO | 14.0 |
| Cocamidopropylbetaine | 1.6 |
| Jaguar C17[1] | 0.2 |
| Glydant[2] | 0.2 |

[1] is Guar Hydroxypropyltrimonium Chloride
[2] is DMDM Hydantoin

To this base shampoo was added the following:
Example A—0.5 wt % palmitoyl ethanolamide
Example B—1.0 wt % palmitoyl ethanolamide
Example 1—1.0% palmitoyl ethanolamide eutectic mixture containing a 1:1:1 molar ratio of palmitoyl ethanolamide/menthol/salicylic acid (0.5 wt % palmitoyl ethanolamide/0.26 wt % menthol/0.24 wt % salicylic acid).

Quantification of the analyte, palmitoyl ethanolamide, was carried out using reverse phase chromatography on an Agilent 1100 LCMS utilising palmitoyl ethanolamide deposition in vitro was determined by ethanol extraction of the compound from an artificial skin model (Vitro-Skin™, representative of the scalp skin), followed by HPLC measurement. Quantitation was made by reference to a standard curve. Pre-cut artificial skin was sandwiched in a plastic ring support, with its rough topography facing up. Water (1.5 ml) was added to the plastic ring, followed by 0.5 ml of shampoo base, containing palmitoyl ethanolamide alone, or the eutectic mixture (see above). The mixture was then stirred with a teflon stirring rod, ensuring contact with the artificial skin surface, so as to mimic the massaging of the scalp by a consumer during hair washing. The shampoo solution was removed from the plastic ring with a dropper, ensuring that no liquor remained, and the artificial skin rinsed with 2 ml of distilled water, including 30 s of stirring as before. The rinsing water was then removed. Palmitoyl ethanolamide extraction was performed with ethanol (100%, 3 ml) with 30 s stirring. The resulting supernatant was filtered through a 0.45 µm PTFE filter into a standard HPLC vial.

Quantification of the analyte, palmitoyl ethanolamide, was carried out using reverse phase chromatography on an Agilent 1100 LCMS utilising an electrospray ionisation source. A deuterated form of the analyte was used as an internal standard and added to both the samples and calibration standards prior to injection using Agilent 1100 autosampler. The palmitoyl ethanolamide concentration (ppm) was measured from the generated standard calibration curves.

Table 1 demonstrates the effect of a eutectic shampoo formulation containing a 1:1:1 molar ratio of palmitoyl ethanolamide/menthol/salicylic acid on the deposition of palmitoyl ethanolamide. All actives were formulated in the shampoo formulation of formula 1. Note that the eutectic formulation contains only 0.5% palmitoyl ethanolamide (and 0.26 wt % menthol and 0.24 wt % salicylic acid), but delivers a 3-fold improvement in palmitoyl ethanolamide deposition efficiency. This shows that the eutectic formulation enhances the amount of palmitoyl ethanolamide available for deposition from the shampoo formulation.

TABLE 1

| Example | Formulation | Deposited ppm | Deposited % Efficiency | S.D. |
|---|---|---|---|---|
| A | 0.5% PMEA | 1.92 | 0.08 | 0 |
| B | 1% PMEA | 4 | 0.08 | 0.06 |
| 1 | 1% PMEA Eutectic mix | 5.6 | 0.22 | 0.09 |

The invention claimed is:

1. A personal care composition having an aqueous base comprising a eutectic mixture, the eutectic mixture comprising the CB receptor activating agent palmitoylethanolamide; wherein presence of mixture is demonstrated by decrease in melting temperature of the mixture relative to that of the melting temperatures of the individual constituent actives.

2. A personal care composition according to claim 1 which is a hair care composition.

3. A personal care composition according to claim 1 in which the eutectic mixture comprises menthol.

4. A personal care composition according to claim 1 in which the eutectic mixture comprises an organic acid.

5. A personal care composition according to claim 4 in which the organic acid is selected from the list consisting of salicylic acid, benzoic acid, and mixtures thereof.

6. A personal care composition according to claim 4 in which the molar ratio of palmitoyl ethanolamide/menthol/organic acid within the eutectic mixture is from 0.1:1:1 to 2:1:1.

7. A personal care composition according to claim 1 in which the eutectic mixture has a melting point below 45° C.

8. A personal care composition according to claim 1 in which the level of eutectic mixture is from 0.01 to 5 wt % of the total composition.

9. A personal care composition according to claim 1 which further comprises at least 2 wt % of the total composition of a surfactant.

10. A personal care composition according to claim 9 in which the surfactant is an anionic surfactant.

11. A method of depositing a CB receptor activating agent palmitoylethanolamide onto the scalp or skin in which the CB receptor activating agent is in the form of a eutectic mixture.

12. A method of mitigating scalp itch comprising the step of applying to the hair and/or scalp a composition according to claim 1.

\* \* \* \* \*